(12) United States Patent
Parker et al.

(10) Patent No.: US 6,835,719 B2
(45) Date of Patent: Dec. 28, 2004

(54) PESTICIDAL COMPOSITION

(75) Inventors: Diana L. Parker, Brentwood Bay (CA); George S. Puritch, Saanichton (CA); David S. Almond, Victoria (CA); Frederick S. Sedun, Saanichton (CA); Cameron D. Wilson, Victoria (CA)

(73) Assignee: W. Neudorff GmbH KG (DE)

( * ) Notice: Subject to any disclaimer, the term of this patent is extended or adjusted under 35 U.S.C. 154(b) by 4 days.

(21) Appl. No.: 10/323,539

(22) Filed: Dec. 18, 2002

(65) Prior Publication Data

US 2003/0138500 A1 Jul. 24, 2003

Related U.S. Application Data

(60) Provisional application No. 60/341,941, filed on Dec. 19, 2001.

(51) Int. Cl.[7] .................. A01N 65/00; A01N 43/08; A61K 31/40; A61K 31/215; A61K 31/135
(52) U.S. Cl. ................ 514/65; 514/421; 514/461; 514/468; 514/529; 514/531; 514/534; 514/540; 514/658
(58) Field of Search ................... 514/65, 421, 461, 514/468, 529, 531, 534, 540, 658

(56) References Cited

U.S. PATENT DOCUMENTS

| | | | |
|---|---|---|---|
| 4,094,969 A | | 6/1978 | Batzer et al. |
| 5,192,793 A | | 3/1993 | Szekely et al. |
| 5,631,285 A | | 5/1997 | Kataoka et al. |
| 6,090,415 A | * | 7/2000 | Stadler et al. ............ 424/713 |

FOREIGN PATENT DOCUMENTS

| | | | |
|---|---|---|---|
| EP | 1057406 | | 12/2000 |
| GB | 1159137 | * | 7/1969 |
| WO | WO 00/54591 | | 9/2000 |

OTHER PUBLICATIONS

Bonide Garden Dust product label.
Letter to James J. Wurtz regarding Bonide Garden Dust EPA Registration, dated Aug. 19, 1991.
George N. Agrios, "Direct Protection by Chemical Controls," Plant Pathology, pp. 209, Fourth Edition, Academic Press.
"Disease Prevention and Control," The Organic Gardener's Handbook of Natural Insect and Disease Control, pp. 369, Rodale Press, Emmaus, Pennsylvania.
Formulating Pyrethrum, pp. 30, issued by the Pyrethrum Bureau Nakuru, Kenya.
William Olkowski, Sheila Daar, and Helga Olkowski, "Chapter 7: Inorganics, Organics and Botanicals," pp. 109, Common Sense Pest Control, The Taunton Press.

* cited by examiner

Primary Examiner—Alton Pryor
(74) Attorney, Agent, or Firm—Nutter McClennen & Fish LLP

(57) ABSTRACT

An environmentally safe pesticidal liquid suspension composition including a mixture of sulfur combined with pyrethrins and/or pyrethroids is provided. The pesticidal composition is effective to control plant diseases, as well as insect and mite pests. The composition can be prepared as concentrated or ready-to-use formulations. Formulations can be applied to plants, both indoors and outdoors, to control plant disease and insect and mite pests and reduce plant damage from such pests. The formulations can be applied to plants with minimal phytotoxicity (plant damage) and do not leave unacceptable levels of visible sulfur residue.

46 Claims, No Drawings

PESTICIDAL COMPOSITION

CROSS-REFERENCE TO RELATED APPLICATIONS

This application claims priority from U.S. Provisional Patent Application Ser. No. 60/341,941, filed on Dec. 19, 2001, entitled "Pesticidal Composition," which is expressly incorporated by reference herein.

FIELD OF THE INVENTION

The present invention relates to environmentally safe pesticides, and more particularly, to a pesticide formulation containing sulfur combined with pyrethrins and/or pyrethroids for the control of plant diseases, insect pests, and mite pests.

BACKGROUND OF THE INVENTION

With the rising concern about environmental safety there has been a renewed interest in the use of naturally occurring substances, including plant oils and their derivatives, as pesticides. Substances such as pyrethrins derived from chrysanthemum flowers, azadirachtin from the neem tree, and rotenone from derris roots have become popular control actives for a variety of insect pests. Pyrethrum extract, obtained from *Chrysanthemum cinerariaefolium*, contains several esters that are very effective insecticides against a wide range of insect pests. These esters, collectively called pyrethrins, are the most common botanical pesticides in the lawn and garden pesticide market. The pyrethrins are contact insecticides, causing rapid knockdown and mortality of insects at very low concentrations. These features and their relatively safe mammalian toxicological profile have contributed to the success in the marketplace and allowed them to compete against synthetic hydrocarbons. Synthetic synergists, such as piperonyl butoxide (PBO), are commonly used to enhance insecticidal activity in commercial formulations of insecticides especially pyrethrum extract and pyrethroids. However, with the increased interest in organic gardening and recent official organic certification procedures, there has been a desire to utilize only natural constituents in pesticide formulations.

Pyrethroids are synthetic analogues of pyrethrins. They are often more toxic and last longer in the environment than pyrethrins. Pyrethroids are effective against a wide range of insects. Of the more than 1000 pyrethroids developed, about 10 are currently used in the United States. Pyrethroids are classified as Type I or Type II based on differences in basic structure and poisoning symptoms.

Sulfur, which is one of the oldest fungicides known, is also widely used today as a pesticide for the control of powdery mildews, rusts, leaf blights and fruit rots. Agrios, G. N., Plant Pathology, 4th edition, p. 208. Sulfur disrupts the metabolic processes of fungi and protects plants from disease by inhibiting spore germination. Ellis, B. W. and F. Marshall Bradley, eds., Natural Insect and Disease Control, p. 369. Sulfur is also sometimes used as a miticide. For example, Kumulus D F, a water dispersible granular fungicide, is an approved pesticide for use against rust mites. Problems associated with sulfur formulations include unsightly residue on ornamentals and the tendency of sulfur to settle out when in liquid form. Olkowski, W. et al, Common Sense Pest Control, p. 109. Some plants are sensitive to sulfur and plant damage can occur when temperatures during application are greater than 30° C.

In recent years, consumers have sought less time-consuming ways to apply pesticides. As a result, ready-to-use formulations that require no mixing are now very popular. Moreover, many consumers would also prefer to have one product that controls all pest-related problems on their plants, rather than having to make a separate application with a different product for each problem. While some combination products are currently marketed for the control of fungi, insects and diseases, these products are not always effective against all three target groups.

Accordingly, there exists a need for effective, environmentally safe, easy to use insecticides for simultaneous control of plant diseases and insect and mite pests.

SUMMARY OF THE INVENTION

The present invention is directed to an environmentally safe pesticidal liquid suspension composition including a mixture of sulfur combined with pyrethrins and/or pyrethroids. The composition can also optionally include an antioxidant. In use, the pesticidal composition is effective to control plant diseases, as well as insect and mite pests.

The composition can be prepared as a concentrate or a ready-to-use formulation. Formulations can be applied to plants, both indoors and outdoors, to control plant disease and insect and mite pests, and to reduce plant damage from such pests. The formulations can be applied to plants with minimal phytotoxicity and do not leave unacceptable levels of visible sulfur residue.

Unless otherwise noted, all percentages referred to herein are percent by weight.

DETAILED DESCRIPTION OF THE INVENTION

Pyrethrins are incompatible with many compounds and are readily degraded. Oxidation, alkaline hydrolysis and breakdown by microbes are all common modes of degradation. Degradation makes formulations containing pyrethrins, particularly water-based formulations, difficult to stabilize. Anaerobic bacteria are commonly found in sulfur formulations and can further increase the likelihood of pyrethrins degradation. The chemical nature of sulfur and pyrethrins have prevented and/or discouraged a liquid formulation containing these two substances. Sulfur could even actually accelerate the degradation of pyrethrins. Since pyrethrum extract is oil soluble or lipophylic, it must be emulsified to add into a liquid system. Sulfur, on the other hand, is a particulate and as a result requires suspension in a liquid system. Not only is it difficult to combine a particulate fungicide with an oil-based insecticide, there are additional problems associated with combining sulfur with any oil based active ingredient. Oil is known to increase sulfur phytotoxicity. As a result, commercial sulfur labels contain cautions against mixing sulfur with oil and carry warnings such as: "do not use within 30 days of an oil spray and do not mix with oil."

In general, the present invention provides effective, environmentally safe, easy to use, liquid suspension pesticide formulations for the control of diseases, and insect and mite pests on plants. The pesticide formulation includes a mixture of sulfur combined with pyrethrins and/or pyrethroids, the combination of which is particularly advantageous in controlling plant diseases, as well as combating insect and mite pests. The composition also preferably includes antioxidants, which are effective to stabilize the formulation.

Three types of sulfur formulations are generally available: sulfur dust, wettable sulfur and colloidal sulfur. Wettable sulfur, which consists of finely ground sulfur particles and a wetting agent, is available in two types of formulations: wettable powder and water dispersible granule formulations. Colloidal sulfur, which consists of very small particle sizes which are formulated as a wet paste, is available in a liquid flowable formulation. The present invention preferably utilizes wettable powder, water dispersible granules, and liquid flowable sulfur formulations. An example of a water dispersible granule is Kumulus from BASF Corp., Mount Olive, N.J., and a wettable powder is Suffa WP 90 from Drexel. Examples of liquid flowable formulations include Red Ball Sulfur from International Sulfur Inc., Mt. Pleasant, Tex., and THAT sulfur from Stoller's Chemical Co., Houston, Tex.

The sulfur active ingredient is preferably used at an end-use concentration in the range of about 0.025% to 1.0% (250 to 10,000 ppm), and more preferably at a concentration in the range of about 0.2% to 0.4% (2000 to 4000 ppm). Concentrated formulations obviously have higher levels of active ingredients but are typically diluted prior to use. Depending on the dilution rate, concentrates may contain in the range of about 2% sulfur to 40% sulfur (20,000 to 400,000 ppm ai sulfur), preferably within the range of about 4% sulfur and 20% sulfur (40,000 to 200,000 ppm ai sulfur). Based on the disclosure that follows, one of ordinary skill in the art will readily appreciate that the concentration of sulfur may vary somewhat depending on the target pest, mode of application and application rate.

As previously stated, the composition further includes a second component which can be pyrethrins, pyrethroids, or combinations thereof. A variety of suitable pyrethrum extracts can be used as suitable sources of pyrethrins according to the present invention. Pyrethrum extracts are plant products obtained from dried flowers of *Chrysanthemum cinerariaefolium*. The principal parts of the flower from which pyrethrum extracts are derived include the achenes, petals, receptacles, scales, and disc florets. Pyrethrum extracts are commercially available from a number of sources including the Pyrethrum Marketing Board of Kenya and MGK Company of Minneapolis, Minn. The active ingredients of pyrethrum extracts are collectively referred to as "pyrethrins." Pyrethrins include pyrethrin I, pyrethrin II, cinerin I, cinerin II, jasmolin I and jasmolin II. The total pyrethrins component of commercially available pyrethrum extracts typically is in the range of about 15 to 65%. More commonly, pyrethrum extracts are utilized with a total pyrethrin content in the range of about 20 to 50% by weight.

Both Type I and Type II pyrethroids can be used as suitable sources of pyrethroids according to the present invention. Examples of Type I pyrethroids include Allethrin, Bifenthrin, Permethrin, Phenothrin, Resmethrin and Tetramethrin. Examples of Type II pyrethroids include Deltamethrin, Fenvalerate and Fluvalinate. Permethrin is one of the most common pyrethroids and is sold under several trade names including Ambush and Pounce. Pyrethroids are produced by many different companies including ICI Agricultural Products, Fairfield American Corporation and MGK Company of Minneapolis, Minn.

The pyrethrin active ingredient (ai) is preferably used at an end-use concentration, e.g., in a ready-to-use formulation or a diluted concentrate formulation, in the range of about 25 ppm ai to 1000 ppm ai pyrethrins component (0.0025% to 0.1%), and more preferably at a concentration in the range of about 50 to 200 ppm ai pyrethrins component (0.005% to 0.02%). Concentrated formulations obviously have higher levels of active ingredient, but are typically diluted prior to use. Depending on the dilution rate, concentrates may contain in the range of about 0.05% pyrethrins to 1.0% pyrethrins (500 to 10,000 ppm ai pyrethrins), preferably within the range of about 0.1% pyrethrins and 0.5% pyrethrins (1000 to 5000 ppm ai pyrethrins). Based on the disclosure that follows, one of ordinary skill in the art will readily appreciate that the concentration of the pyrethrins may vary somewhat depending on the target pest, mode of application and application rate. Higher than necessary concentrations may also be applied where a residual or longer lasting pesticidal effect is desired.

The synthetic pyrethroid active ingredient is preferably used at an end-use concentration in the range of about 10 ppm ai to 400 ppm ai pyrethroid component (0.001% to 0.04%), and more preferably at a concentration in the range of about 20 to 250 ppm ai pyrethroid component (0.002% to 0.025%). Concentrated formulations obviously have higher levels of active ingredient, but are typically diluted prior to use. Depending on the dilution rate, concentrates may contain in the range of about 0.02% pyrethroids to 1.0% pyrethroids (200 to 10,000 ppm ai pyrethroids), preferably within the range of about 0.04% pyrethroids and 0.5% pyrethroids (400 to 500 ppm ai pyrethroids). Based on the disclosure that follows, one of ordinary skill in the art will readily appreciate that the concentration of the pyrethroids may vary somewhat depending on the target pest, mode of application and application rate. Higher than necessary concentrations may also be applied where a residual or longer lasting pesticidal effect is desired.

As previously stated above, the composition also preferably include one or more antioxidants. Antioxidants can be useful additives in the composition in order to reduce the effect of oxidation of the pyrethrins. Sulfur can accelerate the degradation of pyrethrins/pyrethroids, thus antioxidants are effective to stabilize the formulation. Examples of suitable antioxidants include butylated hydroxytoluene (BHT), butylated hydroxy anisole (BHA), propyl gallate, and natural antioxidants such as Vitamin E, mixed tocopherols, α-tocopherol, ethoxyquin and ascorbic acid. In an exemplary embodiment, the composition includes an antioxidant present at a concentration in the range of about 0.001% to 2.0%. In an exemplary embodimentthe antioxidant is present at a concentration in the range of about 0.001% to 0.5% in a ready-to-use formulation, and is present at a concentration in the range of about 0.01% o 2.0% in a concentrated formulation.

While the above components are the active ingredients of the composition, other components such as surfactants, suspending agents, preservatives, odor masking agents, and chelating agents can be added to the composition. Surfactants, including emulsifiers, allow mixing of lipophilic compounds into the water carrier and influence spreading on leaf and pest surfaces. Suspending agents, preservatives and chelating agents are used to enhance the physical and chemical stability of the composition.

Surfactants are useful in the composition of the present invention since they are effective to emulsify (mix) the pyrethrum extract and/or pyrethroid with the water component in the formulation. Surfactants are also effective to ensure that the formulation sprays easily and is distributed and spread sufficiently onto the target plant surfaces. A variety of surfactants can be used in a composition according to the present invention, including anionic surfactants, cationic surfactants, nonionic surfactants, amphoteric surfactants, and combinations thereof. Preferably, the surfactant(s) are capable of emulsifying pyrethrins without causing phytotoxicity. Preferred nonionic surfactants include ethoxylated sorbitan derivatives, ethoxylated fatty acids, and mixtures thereof. Exemplary ethoxylated sorbitan derivatives include TWEEN surfactants available from Uniqema (ICI Surfactants), Wilmington, Del. Other suitable sorbitan derivatives include Cirrasol G-1086 from Uniqema (ICI Surfactants), Wilmington, Del., and Emsorb surfactants from Henkel Corp., Cincinnati, Ohio. Other useful surfactants include fatty acid salts such as potassium oleate and potassium coconate soaps. One of ordinary skill in the art will readily appreciate that such fatty acid salts may be prepared by saponification of fatty acids.

The composition can also include chelating agents, which are useful for sequestering metal ions that catalyze oxidation reactions. Examples of suitable chelators include ethylenediamine tetraacetic acid (EDTA), or derivatives thereof, including sodium, potassium or calcium salts of EDTA. Other suitable chelators include polyphosphate chelators such as sodium tripolyphosphate and natural compounds such as citric and ascorbic acid.

Suspending agents may desirably be added to improve the stability and shelf life of the composition. Examples of suitable suspending agents include gum arabic, guar gum, sodium caseinate, polyvinyl alcohol, magnesium aluminum silicate (e.g., Van Gel B® provided by R. T. Vanderbilt Co. Inc., Norwalk, Conn.), locust bean gum, xanthan gum, kelgum, cellulose derivatives, and mixtures thereof. The composition can also includes thickeners, including, for example, polyacrylic acid polymers such as Pemulen® and Carbopol® provided by B F Goodrich Corp., Brecksville, Ohio.

Preservatives such as microbial control agents may also be useful additives to the composition in order to control the undesirable growth of bacteria and fungi in formulations. Examples of suitable microbial control agents include alcohols, such as ethanol and isopropyl alcohol, benzoic acid, salts of benzoic acid, propionic acid, salts of propionic acid, sorbic acid, salts of sorbic acid, parabens, benzisothiazolin-3-one preservatives (e.g., Proxel® provided by Zeneca of Wilmington, Del.), isothiazolin-3-one preservatives (e.g., Legend® provided by Rohm and Haas of Philadelphia, Pa.), 1-(3-chloroallyl)-3,5,7-triaza-1-azoniaadamantane chloride preservatives (e.g., Dowicil® preservatives provided by Dow Chemicals of Midland, Mich.), and sodium salt of o-phenylphenol preservatives (e.g., Dowicide® preservatives provided by Dow Chemicals of Midland, Mich.).

Solvents are also used and may include water, ethanol, isopropyl alcohol, glycerol, propylene glycol, or other water miscible solvents. The solvents may be used alone or in combination with one another.

The pH of the sulfur/pyrethrins liquid suspension composition influences chemical and physical stability. Ideally, the composition has a pH in the range of about pH 3 to pH 9. After formulation preparation, the pH is measured and adjusted if necessary. Basic formulations would be adjusted using an acid such as hydrochloric acid (HCl). Formulations with pH values below 3 would be adjusted using a base such as sodium hydroxide (NaOH).

The insecticidal composition of the invention can be prepared in various forms, including as sprayable liquids and aerosols. A sprayable liquid suspension form is preferred. Liquid suspension compositions may be prepared in a concentrated form or in a ready-to-use form.

The composition may be applied in areas that are infested with insect and mite pests, garden areas, and on or around trees, plants, and shrubs. The composition exhibits low phytotoxicity and thus may be applied to a variety of plants, flowers, trees, shrubs, and grasses. Since the composition is substantially nontoxic to humans or animals, the composition can be applied in domestic areas, including in and around dwellings.

The composition of the present invention is effective against a wide range of insect and mite pests including, but not limited to, aphids, leafhoppers, whitefly, sawfly larvae, caterpillars, beetles, spider mites and rust mites. The composition is also effective against many plant diseases including but not limited to powdery mildew, rose blackspot, apple scab, leaf blights, rusts and fruit rots.

The following non-limiting examples serve to further describe the invention.

EXAMPLE 1

Preparation of Formulations (Ready-to-Use and Concentrate)

For a ready-to-use liquid suspension formulation, thickeners (Van Gel B+Xanthan gum) are dissolved in water and then sulfur (Red Ball) is added. Liquid pyrethrum extract and a surfactant (Tween 81) are added into a separate vessel containing an antioxidant (BHT) dissolved in a solvent (IPA). Finally, the pyrethrins mixture is added into the sulfur mixture and stirred for several minutes. If necessary, the pH is adjusted to a range of about pH 3 to pH 9 with HCl or NaOH.

For a liquid suspension concentrate formulation, a thickener (Van Gel B) is added to water and high shear mixed for several minutes. A preservative (sodium propionate) followed by a mixture of pyrethrum extract and surfactant (Cirrasol 1086) are then added. Sulfur (Red Ball) is next added to the main vessel. Finally, an antioxidant (BHT) in solvent (IPA) and a gum (Xanthan gum) in solvent (propylene glycol) are added to the main vessel and the batch is stirred for about an hour. If necessary, the pH is adjusted to a range of about pH 3 to pH 9 with HCl or NaOH.

TABLE 1

Formulation specifications

| Ingredients | Concentrate (wt. %) | RTU (wt. %) |
|---|---|---|
| Red Ball Sulfur 53% | 18.88 (10 ai)) | 0.38 (0.20 ai) |
| Pyrethrum Extract (20% ai pyrethrins) | 1.25 (0.25 ai) | 0.05 (0.01 ai) |
| BHT | 0.05 | 0.01 |
| Cirrasol 1086 | 3.00 | — |
| Xanthan gum | 0.20 | 0.05 |
| Van Gel B | 1.00 | 0.25 |
| Propylene glycol | 2.00 | — |
| IPA | 5.00 | 5.00 |
| Sodium propionate | 3.00 | — |
| Tween 81 | — | 0.20 |

EXAMPLE 2

Efficacy Against Twospotted Spider Mites

Adult twospotted spider mites, *Tetranychus urticae* Koch, were obtained from a colony and 25 mites per leaf were placed on bush bean plants (one leaf per replicate). Mites were allowed to settle overnight and then treatments were applied to wetting on top and bottom leaf surfaces using a hand-held trigger sprayer. After treatment, plants were randomized on a lab bench in a randomized block design. Treatments consisted of 9 replicates of 1 plant each. Mortality was assessed 2 days following treatment.

TABLE 2

Mortality of adult female twospotted spider mites two days after treatment.

| Treatment[1] | Observed % Mortality | Expected % Mortality |
|---|---|---|
| 1. Sulfur/pyrethrins RTU (100 ppm ai pyrethrins, 0.2 wt. % ai sulfur) | 58.6 | 17.7 |
| 2. Sulfur/pyrethrins RTU (50 ppm ai pyrethrins, 0.2 wt. % ai sulfur) | 60.2 | 18.2 |
| 3. Sulfur RTU (no pyrethrins, 0.2% ai sulfur) | 46.1 | — |
| 4. Emulsified pyrethrum extract (100 ppm ai pyrethrins) | 13.2 | — |
| 5. Emulsified pyrethrum extract (50 ppm ai pyrethrins) | 13.7 | — |
| 6. Powdered Sulfur (0.2% ai sulfur) | 4.5 | — |
| 7. Distilled water | 3.9 | — |

[1]The Expected Mean % Mortality is based on the sum of mortality for emulsified pyrethrum extract plus Red Ball Sulfur.

Sulfur/pyrethrins ready-to-use (RTU) formulations resulted in slightly higher twospotted spider mite mortalities than the sulfur RTU without pyrethrins. All sulfur/pyrethrins RTU formulations showed synergy compared to the sum of the mortalities for emulsified pyrethrum extract and powdered sulfur alone at equivalent concentrations.

EXAMPLE 3

Efficacy Against Twospotted Spider Mites

Adult twospotted spider mites, *Tetranychus urticae* Koch, were obtained from a colony and 25 mites per leaf were placed on bush bean plants (one leaf per replicate). Mites were allowed to settle overnight and then treatments were applied to wetting on top and bottom leaf surfaces using a hand-held trigger sprayer. After treatment, plants were randomized on a lab bench in a randomized block design. Treatments consisted of 9 replicates of 1 plant each. Mortality was assessed 2 days following treatment.

TABLE 3

Mortality of twospotted spider mites two days after treatment.

| Treatment[1] | Observed % Mortality | Expected % Mortality |
|---|---|---|
| 1. Sulfur/pyrethrins RTU (100 ppm ai pyrethrins, 0.2 wt. % ai sulfur) | 75.9 | 24.5 |
| 2. Sulfur/pyrethrins RTU (50 ppm ai pyrethrins, 0.2 wt. % ai sulfur) | 70.4 | 22.0 |
| 3. Sulfur RTU (no pyrethrins, 0.2% ai sulfur) | 61.7 | — |
| 4. Emulsified pyrethrum extract (100 ppm ai pyrethrins) | 21.9 | — |
| 5. Emulsified pyrethrum extract (50 ppm ai pyrethrins) | 19.4 | — |
| 6. Powdered Sulfur (0.2% ai sulfur) | 2.6 | — |
| 7. Distilled water | 1.0 | — |

[1]The Expected Mean % Mortality is based on the sum of mortality for emulsified pyrethrum extract plus Red Ball Sulfur.

Sulfur/pyrethrins ready-to-use (RTU) formulations resulted in slightly higher twospotted spider mite mortalities than the sulfur RTU without pyrethrum extract. All sulfur/pyrethrins RTU formulations showed synergy compared to the sum of the mortalities for powdered sulfur and emulsified pyrethrum extract alone at equivalent concentrations.

EXAMPLE 4

Efficacy Against Green Peach Aphids

Radish plants were placed in a colony for 4 days for infestation with green peach aphid, *Myzus persicae* (Sulzer). Treatments were then applied with a hand-held trigger sprayer to wetting on all leaf surfaces. After treatment, plants were randomized on a lab bench in a completely randomized block design. Treatments consisted of 8 replicates of 1 plant each. Mortality was assessed after 2 days by counting the live and dead aphids on all leaves.

TABLE 4

Mortality of green peach aphids after 2 days.

| Treatment[1] | Observed Mean % Mortality | Expected Mean % Mortality |
|---|---|---|
| 1. Sulfur/pyrethrins RTU (100 ppm pyrethrins, 0.2 wt. % ai sulfur) | 98.4 | 98.0 |
| 2. Sulfur/pyrethrins RTU (50 ppm pyrethrins, 0.2 wt. % ai sulfur) | 91.0 | 73.0 |
| 3. Sulfur/pyrethrins concentrate (1:50) (50 ppm ai pyrethrins, 0.2% ai sulfur) | 67.3 | — |
| 4. Sulfur/pyrethrins concentrate (1:25) (100 ppm ai pyrethrins, 0.4% ai sulfur) | 65.8 | — |
| 5. Sulfur RTU (no pyrethrins, 0.2% ai sulfur) | 33.8 | — |
| 6. Emulsified pyrethrum extract (100 ppm pyrethrins) | 96.7 | — |
| 7. Emulsified pyrethrum extract (50 ppm pyrethrins) | 71.7 | — |
| 8. Powdered Sulfur (0.2% ai sulfur) | 1.3 | — |
| 9. Distilled water | 0.0 | — |

[1]The Expected Mean % Mortality is based on the sum of mortality for emulsified pyrethrum extract plus Red Ball Sulfur.

High mortalities were observed with all sulfur/pyrethrins ready-to-use (RTU) formulations against green peach aphids. A sulfur RTU without pyrethrum extract was significantly less efficacious. At 50 ppm ai pyrethrins, the sulfur/pyrethrins RTU formulation showed synergy compared to the sum of the mortalities for powdered sulfur and emulsified pyrethrum extract alone at equivalent concentrations.

EXAMPLE 5

Efficacy Against Tobacco Aphids

Radish plants were placed in a colony for 6 days for infestation with tobacco aphid, *Myzus nicotianae* (Blackman). Treatments were then applied with a hand-held trigger sprayer to wetting on all leaf surfaces. After treatment, plants were randomized on a lab bench in a completely randomized block design. Treatments consisted of 10 replicates of 1 plant each. Mortality was assessed after 2 days by counting the live and dead aphids on all leaves.

TABLE 5

Mortality of apterous tobacco aphids on radish plants 2 days after treatment.

| Treatment | Observed Mean % Mortality |
|---|---|
| 1. Sulfur/pyrethrins concentrate (100 ppm ai pyrethrins, 0.4 wt. % ai sulfur) | 95.4 |
| 2. Sulfur/pyrethrins concentrate (50 ppm ai pyrethrins, 0.2 wt. % ai sulfur) | 91.4 |

TABLE 5-continued

Mortality of apterous tobacco aphids on radish plants 2 days after treatment.

| Treatment | Observed Mean % Mortality |
| --- | --- |
| 3. Insecticidal Soap (1 in 50 dilution rate) | 83.5 |
| 5. Distilled water | 1.4 |

High mortalities were observed with the sulfur/pyrethrins concentrates against tobacco aphids. Insecticidal Soap resulted in lower mortalities. No phytotoxicity was observed on radish plants treated with the sulfur/pyrethrins formulations.

EXAMPLE 6
Efficacy Against Rose Sawfly Larvae

Rose sawfly larvae (rose slugs), *Endelomyia aethiops* (Fabricus), were collected from rose plants. For treatment, larvae were placed on styrofoam plates and treatments were applied with a hand-held trigger sprayer (two passes per replicate). After spraying, all insects were transferred onto paper towel prior to placement in petri dishes containing moistened filter paper and a rose leaf as a food source. Treatments consisted of 2 replicates of 1 larva each. Mortality was assessed one day following treatment.

TABLE 6

Mortality of rose sawfly larvae one day after treatment.

| Treatment | Mean % Mortality |
| --- | --- |
| 1. Sulfur/pyrethrins RTU (50 ppm ai pyrethrins, 0.2% ai sulfur) | 100.0 |
| 2. Distilled water | 0.0 |

Complete mortality (100%) of rose sawfly larvae was observed after direct contact with a sulfur/pyrethrins ready-to-use (RTU) formulation.

EXAMPLE 7
Powdery Mildew Disease Control on Roses

Miniature rose plants susceptible to powdery mildew ('Little White Lies' variety) were treated weekly for a total of 14 applications with treatments using hand trigger sprayers. Plants were fertilized regularly to promote vigorous growth. Each treatment consisted of four replicates. Assessments were made using a rating scale of 0 to 10, with 0 representing no powdery mildew and 10 representing complete coverage with powdery mildew.

TABLE 7

Powdery mildew rating on rose plants treated weekly.

| Treatment | Powdery Mildew Rating |
| --- | --- |
| 1. Sulfur RTU (no pyrethrins, 0.2% ai sulfur) | 1.5 |
| 2. Sulfur/pyrethrins RTU (100 ppm ai pyrethrins, 0.2 wt. % sulfur) | 1.1 |
| 3. Safer's Sulfur Garden Fungicide | 1.5 |
| 4. Orthenex 3 in 1 product (4% Acephate + 3.25% Triforine + 0.75% Hexakis) | 2.4 |
| 5. Untreated control | 7.6 |

All treatments resulted in significantly less powdery mildew than the untreated control treatment. The sulfur/pyrethrins ready-to-use (RTU) treatment resulted in the lowest level of powdery mildew. All sulfur treatments were more effective against rose powdery mildew than the Orthenex 3-in-1 product. Some phytotoxicity was observed with the Safer's Garden Fungicide in the form of marginal necrosis, leaf distortion and chlorosis. No phytotoxicity was observed with the sulfur/pyrethrins RTU.

EXAMPLE 8
Powdery Mildew Disease Control on Zucchini

Treatments were applied to "Zucchini Select" zucchini plants in the field, using a completely randomized experimental design. The plants were sprayed every 7 to 14 days using a hand-pump sprayer, for a total of 9 spray applications. Treatments consisted of 6 replicates of 1 plant each. The plants were assessed periodically for zucchini powdery mildew (*Sphaerotheca fuliginea*) by determining the area colonized on upper leaf surfaces.

TABLE 8

Leaf area colonized by zucchini powdery mildew on treated plants.

| Treatment | Leaf Area Colonized (%) |
| --- | --- |
| 1. Sulfur/pyrethrins RTU (100 ppm pyrethrins, 0.2 wt. % ai sulfur) | 8 |
| 2. Sulfur/pyrethrins concentrate (1:50) (50 ppm ai pyrethrins, 0.2 wt. % ai sulfur) | 2 |
| 3. Sulfur/pyrethrins concentrate (1:25) (100 ppm ai pyrethrins, 0.4 wt. % ai sulfur) | 1 |
| 4. Safer's Sulfur Garden Fungicide | 0 |
| 5. Untreated control | 94 |

Sulfur/pyrethrins formulations effectively controlled powdery mildew on zucchini.

EXAMPLE 9
Rust Disease Control on Currants

Treatments were applied to black currant plants, *Ribes nigrum*, using a completely randomized experimental design. The plants were sprayed every 7 to 14 days using a hand-pump sprayer, for a total of 11 applications. Treatments consisted of 12 replicates of 1 plant each. For assessment, the number of rust sori, *Cronartium occidentale*, was recorded.

TABLE 9

Effect of treatments on currant rust.

| Treatment | Total # Rust Sori (per 12 plants) |
| --- | --- |
| 1. Sulfur/pyrethrins RTU (100 ppm pyrethrins, 0.2 wt. % ai sulfur) | 2 |
| 2. Sulfur/pyrethrins concentrate (1:50) (50 ppm ai pyrethrins, 0.2 wt. % ai sulfur) | 8 |
| 3. Sulfur/pyrethrins concentrate (1:25) (100 ppm ai pyrethrins, 0.4 wt. % ai sulfur) | 1 |
| 4. Safer's Sulfur Garden Fungicide | 7 |
| 5. Untreated control | 3143 |

The sulfur/pyrethrins treatments significantly reduced the number of currant rust sori compared to the untreated control.

EXAMPLE 10
Blackspot Control on Roses

Treatments were applied to 'Altissimo' rose plants in the field, using a completely randomized experimental design.

The plants were sprayed using a hand-pump sprayer every 7 to 14 days, for a total of 15 applications. Treatments consisted of 12 replicates of 1 plant each. Plants were assessed periodically for rose blackspot infection, *Diplocarpon rosae*, by assessing the number of leaves with blackspot and leaf loss.

TABLE 10

Effect of sulfur/pyrethrins treatments on rose blackspot.

| Treatment | Leaves (%) with Blackspot | % Leaf Loss |
| --- | --- | --- |
| 1. Sulfur/pyrethrins RTU (100 ppm pyrethrins, 0.2 wt. % ai sulfur) | 9 | 9 |
| 2. Sulfur/pyrethrins RTU (50 ppm pyrethrins, 0.2 wt. % ai sulfur) | 15 | 8 |
| 3. Sulfur/pyrethrins concentrate (1:50) (50 ppm ai pyrethrins, 0.2 wt. % ai sulfur) | 12 | 9 |
| 4. Sulfur/pyrethrins concentrate (1:25) (100 ppm ai pyrethrins, 0.4 wt. % ai sulfur) | 13 | 9 |
| 5. Safer's Sulfur Garden Fungicide | 12 | 30 |
| 6. Untreated control | 46 | 44 |

The sulfur/pyrethrins ready-to-use and concentrate formulations effectively controlled rose blackspot. Less leaf loss was observed with the sulfur/pyrethrins formulations than with the sulfur only fungicide.

EXAMPLE 11

Efficacy Against Twospotted Spider Mites

Adult twospotted spider mites, *Tetranychus urticae* Koch, were obtained from a colony and 25 mites per leaf were placed on bush bean plants (one leaf per replicate). Mites were allowed to settle overnight and then treatments were applied to wetting on top and bottom leaf surfaces using a hand-held trigger sprayer. After treatment, plants were randomized on a lab bench in a randomized block design. Treatments consisted of 10 replicates of 1 plant each. Mortality was assessed 2 days following treatment.

TABLE 11

Mortality of adult female twospotted spider mites two days after treatment.

| Treatment[1] | Observed % Mortality | Expected % Mortality |
| --- | --- | --- |
| 1. Sulfur/pyrethrins RTU (100 ppm ai pyrethrins, 0.2% ai sulfur) | 95.8 | — |
| 2. Sulfur/permethrin RTU (100 ppm ai permethrin, 0.2 % ai sulfur) | 99.3 | 31.0 |
| 3. Emulsified permethrin (100 ppm ai permethrin) | 26.2 | — |
| 4. Powdered Sulfur (0.4% ai sulfur) | 4.8 | — |
| 5. Distilled water | 4.3 | — |

[1]The Expected Mean % Mortality is based on the sum of mortality for emulsified permethrin plus Red Ball Sulfur.

As shown, high twospotted mite mortalities were observed with both the sulfur/pyrethrins ready-to-use (RTU) formulation and the sulfur/permethrin RTU formulation. The sulfur/permethrin RTU formulation showed synergy compared to the sum of the mortalities for emulsified permethrin and powdered sulfur alone at equivalent concentrations.

EXAMPLE 12

Efficacy Against Green Peach Aphids

Green peach aphids, *Myzus persicae* (Sulzer), were obtained from a colony and transferred to plate glass for treatment. Treatments were then applied with a hand-held trigger sprayer to wetting and aphids remained exposed to treatments for 60 seconds. After treatment, aphids were transferred to filter paper lined petri dishes and dishes were randomized on a lab bench in a completely randomized design. Treatments consisted of 10 replicates of 10 aphids each. Mortality was assessed after 1 day.

TABLE 12

Mortality of green peach aphids after 1 day.

| Treatment[1] | Observed % Mortality | Expected % Mortality |
| --- | --- | --- |
| 1. Sulfur/pyrethrins RTU (100 ppm ai pyrethrins, 0.2% ai sulfur) | 97.0 | — |
| 2. Sulfur/pyrethrins concentrate (1:25) (100 ppm ai pyrethrins, 0.4% ai sulfur) | 100.0 | — |
| 3. Sulfur/permethrin RTU (100 ppm ai permethrin, 0.2% ai sulfur) | 89.0 | 90.0 |
| 4. Sulfur/permethrin concentrate (1:25) (100 ppm ai permethrin, 0.4% ai sulfur) | 88.0 | 90.0 |
| 5. Emulsified permethrin (100 ppm ai permethrin) | 84.0 | — |
| 6. Powdered Sulfur (0.4% ai sulfur) | 6.0 | — |
| 7. Distilled water | 4.0 | — |

[1]The Expected Mean % Mortality is based on the sum of mortality for emulsified permethrin plus Red Ball Sulfur.

High mortalities were observed with all sulfur/pyrethrins and sulfur/permethrin ready-to-use (RTU) and concentrate formulations against green peach aphids.

Those skilled in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A liquid suspension pesticidal composition, consisting essentially of sulfur, a second component selected from the group consisting of pyrethrins, pyrethroids, and combinations thereof, and an antioxidant effective to reduce oxidation of the second component, the composition being environmentally compatible and exhibiting little or no phytotoxicity.

2. The composition of claim 1, wherein the composition is a ready-to-use formulation, and the antioxidant is present at a concentration in the range of about 0.001% to 0.5%.

3. The composition of claim 1, wherein the composition is prepared as a concentrated formulation, and the antioxidant is present at a concentration in the range of about 0.01% to 2.0%.

4. The composition of claim 1, wherein the antioxidant is selected from the group consisting of butylated hydroxytoluene, butylated hydroxy anisole, propyl gallate, and natural antioxidants.

5. The composition of claim 1, wherein the composition is a ready-to-use formulation.

6. The composition of claim 1, wherein the second component is one or more pyrethrins present at a concentration of about 25 ppm to 1000 ppm.

7. The composition of claim 1, wherein the second component is one or more pyrethrins present at a concentration of about 50 to 200 ppm.

8. The composition of claim 1, wherein the second component is a synthetic pyrethroid present at a concentration of about 10 to 400 ppm.

9. The composition of claim 1, wherein the second component is a synthetic pyrethroid present at a concentration of about 20 to 250 ppm.

10. The composition of claim 1, wherein the sulfur is present at a concentration of about 0.025% to 1.0%.

11. The composition of claim 1, wherein the sulfur is present at a concentration of about 0.2% to 0.4%.

12. The composition of claim 1, wherein the composition is a concentrated formulation.

13. The composition of claim 12, wherein the second component is one or more pyrethrins present at a concentration of about 500 ppm to 10,000 ppm.

14. The composition of claim 12, wherein the second component is one or more pyrethrins present at a concentration of about 1000 to 5000 ppm.

15. The composition of claim 12, wherein the second component is a synthetic pyrethroid present a concentration of about 200 to 10,000 ppm.

16. The composition of claim 12, wherein the second component is a synthetic pyrethroid present at a concentration of about 400 to 5000 ppm.

17. The composition of claim 12, wherein the sulfur is present at a concentration of about 2% to 40%.

18. The composition of claim 12, wherein the sulfur is present at a concentration of about 4% to 20%.

19. The composition of claim 1, wherein the sulfur is selected from the group consisting of elemental sulfur, sulfur dust, wettable sulfur, water dispersible granule sulfur, colloidal sulfur, liquid flowable sulfur, and combinations thereof.

20. The composition of claim 1, wherein the composition has a pH in the range of about 3 to 9.

21. The composition of claim 4, wherein the natural antioxidants are selected from the group consisting of Vitamin E, mixed tocopherols, α-tocopherol, ethoxyquin, and ascorbic acid.

22. A liquid suspension pesticidal composition, consisting essentially of sulfur, a second component selected from the group consisting of pyrethrins, pyrethroids, and combinations thereof, an antioxidant effective to reduce oxidation of the second component, the composition being environmentally compatible and exhibiting little or no phytotoxicity, and a surfactant capable of emulsifying the second component without causing phytotoxicity.

23. The composition of claim 22, wherein the surfactant is selected from the group consisting of anionic surfactants, nonionic surfactants, cationic surfactants, amphoteric surfactants, and combinations thereof.

24. A liquid suspension pesticidal composition, consisting essentially of sulfur, a second component selected from the group consisting of pyrethrins, pyrethroids, and combinations thereof, an antioxidant effective to reduce oxidation of the second component, the composition being environmentally compatible and exhibiting little or no phytotoxicity, and a suspending agent effective to suspend the sulfur component in the formulation.

25. The composition of claim 24, wherein the suspending agent is selected from the group consisting of gum arabic, guar gum, sodium caseinate, polyvinyl alcohol, magnesium aluminum silicate, locust bean gum, xanthan gum, kelgum, cellulose derivatives, polyacrylic acid polymers, and mixtures thereof.

26. A liquid suspension pesticidal composition, consisting essentially of sulfur, a second component selected from the group consisting of pyrethrins, pyrethroids, and combinations thereof, an antioxidant effective to reduce oxidation of the second component, the composition being environmentally compatible and exhibiting little or no phytotoxicity, and a microbial preservative selected from the group consisting of benzoic acid, salts of benzoic acid, propionic acid, salts of propionic acid, sorbic acid, salt of sorbic acid, parabens, benzisothiazolin-3-one, isothiazolin-3-one, 1-(3-chloroallyl)-3,5,7-triaza-1-azoniaadamantane chloride, sodium salt of o-phenylphenol, and mixtures thereof.

27. A method for controlling unwanted insect pests, mite pests, and plant diseases, comprising the steps of:
    providing a composition consisting essentially of sulfur, a second component selected from the group consisting of pyrethrins, pyrethroids, and combinations thereof, and an antioxidant effective to reduce oxidation of the second component; and
    applying a pesticidally effective amount of the composition to an area where plant diseases, insect pests, and mite pests are not desired.

28. The method of claim 27, wherein the composition is a ready-to-use formulation, and the antioxidant is present at a concentration in the range of about 0.001% to 0.5%.

29. The method of claim 27, wherein the composition is prepared as a concentrated formulation, and the antioxidant is present at a concentration in the range of about 0.0 1% to 2.0%.

30. The method of claim 27, wherein the antioxidant is selected from the group consisting of butylated hydroxytoluene, butylated hydroxy anisole, propyl gallate, and natural antioxidants.

31. The method of claim 27, wherein the composition is a ready-to-use formulation.

32. The method of claim 31, wherein the second component is one or more pyrethrins present at a concentration of about 25 ppm to 1000 ppm.

33. The method of claim 31, wherein the second component is a synthetic pyrethroid present at a concentration of about 10 to 400 ppm.

34. The method of claim 31, wherein the sulfur is present at a concentration of about 0.025% to 1.0%.

35. The method of claim 27, wherein the composition is prepared as a concentrated formulation.

36. The method of claim 35, wherein the second component is one or more pyrethrins present at a concentration of about 500 ppm to 10,000 ppm.

37. The method of claim 35, wherein the second component is a synthetic pyrethroid present at a concentration of about 200 to 10,000 ppm.

38. The method of claim 35, wherein the sulfur is present at a concentration of about 2% to 40%.

39. The method of claim 27, wherein the sulfur is selected from the group consisting of elemental sulfur, sulfur dust, wettable sulfur, water dispersible granule sulfur, colloidal sulfur, liquid flowable sulfur, and combinations thereof.

40. The method of claim 27, wherein the composition has a pH in the range of about 4 to 9.

41. The method of claim 30, wherein the natural antioxidants are selected from the group consisting of Vitamin E, mixed tocopherols, α-tocopherol, ethoxyquin, and ascorbic acid.

42. A method for controlling unwanted insect pests, mite pests, and plant diseases, comprising the steps of:
    providing a composition consisting essentially of sulfur, a second component selected from the group consisting of pyrethrins, pyrethroids, and combinations thereof, an antioxidant effective to reduce oxidation of the second component, and surfactant capable of emulsifying the second component without causing phytotoxicity; and applying a pesticidally effective amount of the composition to an area where plant diseases, insect pests, and mite pests are not desired.

43. The method of claim 42, wherein the surfactants is selected from the group consisting of anionic surfactants, nonionic surfactants, cationic surfactants, amphoterio surfactants, and combinations thereof.

44. A method for controlling unwanted insect pests, mite pests, and plant diseases, comprising the steps of:

providing a composition consisting essentially of sulfur, a second component selected from the group consisting of pyrethrins, pyrethroids, and combinations thereof, an antioxidant effective to reduce oxidation of the second component, and suspending agent effective to suspend the sulfur component in the formulation; and applying a pesticidally effective amount of the composition to an area where plant diseases, insect pests, and mite pests are not desired.

45. The method of claim 44, wherein the suspending agent is selected from the group consisting of gum arabic, guar gum, sodium caseinate, polyvinyl alcohol, magnesium aluminum silicate, locust bean gum, xanthan gum, kelgum, cellulose derivatives, polyacrylic acid polymers, and mixtures thereof.

46. The method for controlling unwanted insect pests, mite pests, and plant diseases, comprising the steps of:

providing a composition consisting essentially of sulfur, a second component selected from the group consisting of pyrethrins, pyrethroids, and combinations thereof, an antioxidant effective to reduce oxidation of the second component, and a microbial preservative selected from the group consisting of benzoic acid, salts of benzoic acid, propionic acid, salts of propionic acid, sorbic acid, salts of sorbic acid, parabens, benzisothiazolin-3-one isothiazolin-3-one 1-(3-chloroallyl)-3,5,7-triaza-1-azoniaadamantane chloride, sodium salt of o-phenylphenol, and mixtures thereof; and applying a pesticidally effective amount of the composition to an area where plant diseases, insect pests, and mite pests are not desired.

* * * * *